(12) United States Patent
Wang et al.

(10) Patent No.: US 8,219,190 B2
(45) Date of Patent: Jul. 10, 2012

(54) IMPLANTABLE BIOMEDICAL CHIP WITH MODULATOR FOR A WIRELESS NEURAL STIMULATION SYSTEM

(75) Inventors: Chua-Chin Wang, Kaohsiung (TW); Tzung-Je Lee, Kaohsiung (TW)

(73) Assignee: National Sun Yat-Sen University, Kaohsiung (TW)

( * ) Notice: Subject to any disclaimer, the term of this patent is extended or adjusted under 35 U.S.C. 154(b) by 465 days.

(21) Appl. No.: 12/581,915

(22) Filed: Oct. 20, 2009

(65) Prior Publication Data

US 2010/0168828 A1    Jul. 1, 2010

Related U.S. Application Data

(62) Division of application No. 11/352,331, filed on Feb. 13, 2006, now Pat. No. 7,627,371.

(51) Int. Cl.
  *A61N 1/00* (2006.01)
(52) U.S. Cl. ............................................. 607/2; 607/60

(58) Field of Classification Search ..................... 607/32, 607/60
See application file for complete search history.

(56) References Cited

U.S. PATENT DOCUMENTS

| | | | |
|---|---|---|---|
| 5,704,352 A | 1/1998 | Tremblay et al. |
| 6,516,227 B1 | 2/2003 | Meadows et al. |

*Primary Examiner* — Brian T Gedeon
(74) *Attorney, Agent, or Firm* — Volentine & Whitt, PLLC

(57) ABSTRACT

The invention relates to an implantable biomedical chip with modulator for a wireless neural stimulating system. The implantable biomedical chip comprises a power regulator, a demodulator, a baseband circuit, a D/A converter, an instrumentation amplifier, an A/D converter and a modulator. According to the invention, the modulator is mounted on the implantable biomedical chip, and can achieve full-duplex communication to improve the controllability and observability. Besides, the power consumption and area occupation is reduced as compared with using discrete components. Therefore, the integration of the implantable biomedical chip can be easily accomplished.

5 Claims, 6 Drawing Sheets

IMPLANTABLE BIOMEDICAL CHIP WITH MODULATOR FOR A WIRELESS NEURAL STIMULATION SYSTEM

The present application is a divisional of U.S. patent application Ser. No. 11/352,331, now U.S. Pat. No. 7,627,371, filed 13 Feb. 2006.

BACKGROUND OF THE INVENTION

1. Field of the Invention

The present invention relates to an implantable biomedical chip for wireless neural stimulation system, more particularly, an implantable biomedical chip with modulator for a wireless neural stimulating system.

2. Description of the Related Art

Referring to FIG. 1, it shows a conventional wireless neural stimulating system. The conventional wireless neural stimulating system 10 comprises: an internal module 11 and an external module 13. The internal module 11 is implemented in the body. The internal module 11 comprises a receiver coil 111, a voltage rectifier and steps-down circuit 112, a voltage divider 113, a load-shift keying (LSK) modulator 114, a transmitter coil 115 and an implantable biomedical chip 12.

The implantable biomedical chip 12 comprises a power regulator 121, a demodulator 122, a decoder circuit 123, a D/A converter 124, an instrumentation amplifier 125 and an A/D converter 126. The power regulator 121 is used for receiving power from the receiver coil 111 and providing power. The demodulator 122 is used for demodulating an input signal from the receiver coil 111 to a demodulated signal. The decoder circuit 123 is used for decoding the demodulated signal to at least one control signal. The D/A converter 124 is used for converting the control signal to a stimulating current to the nerve. The instrumentation amplifier 125 is used for amplifying and filtering a neural signal from the nerve. The A/D converter 126 is used for converting the neural signal from the instrumentation amplifier to a digital neural signal. The digital neural signal is transmitted to the LSK modulator 114 and is modulated to an output signal. The output signal is transmitted to the external module 13 by the transmitter coil 115.

In the conventional wireless neural stimulating system 10, the LSK modulator 114 is mounted outside the implantable biomedical chip 12. The LSK modulator 114 using discrete components is difficult to be co-simulated with the complete integrated system, and the discrete components occupy larger area on a PCB (printed-circuit board) and have larger power consumption.

Therefore, it is necessary to provide an implantable biomedical chip with modulator for a wireless neural stimulating system to resolve the above problems.

SUMMARY OF THE INVENTION

One objective of the present invention is to provide an implantable biomedical chip with modulator for a wireless neural stimulating system. The implantable biomedical chip comprises a power regulator, a demodulator, a baseband circuit, a D/A converter, an instrumentation amplifier, an A/D converter and a modulator. The power regulator is used for receiving power from a receiver coil and providing power. The demodulator is used for demodulating an input signal from the receiver coil to a demodulated signal. The baseband circuit is used for decoding the demodulated signal to at least one control signal. The D/A converter is used for converting the control signal to a stimulating current. The instrumentation amplifier is used for amplifying and filtering a neural signal. The A/D converter is used for converting the neural signal from the instrumentation amplifier to a digital neural signal. The modulator is used for modulating the digital neural signal to an output signal.

According to the invention, the modulator is mounted on the implantable biomedical chip, and can achieve full-duplex communication to improve the controllability and observability. Besides, the power consumption and area occupation is reduced as compared with using discrete components. Therefore, the integration of the implantable biomedical chip can be easily accomplished.

DETAILED DESCRIPTION OF THE INVENTION

Figure 1:
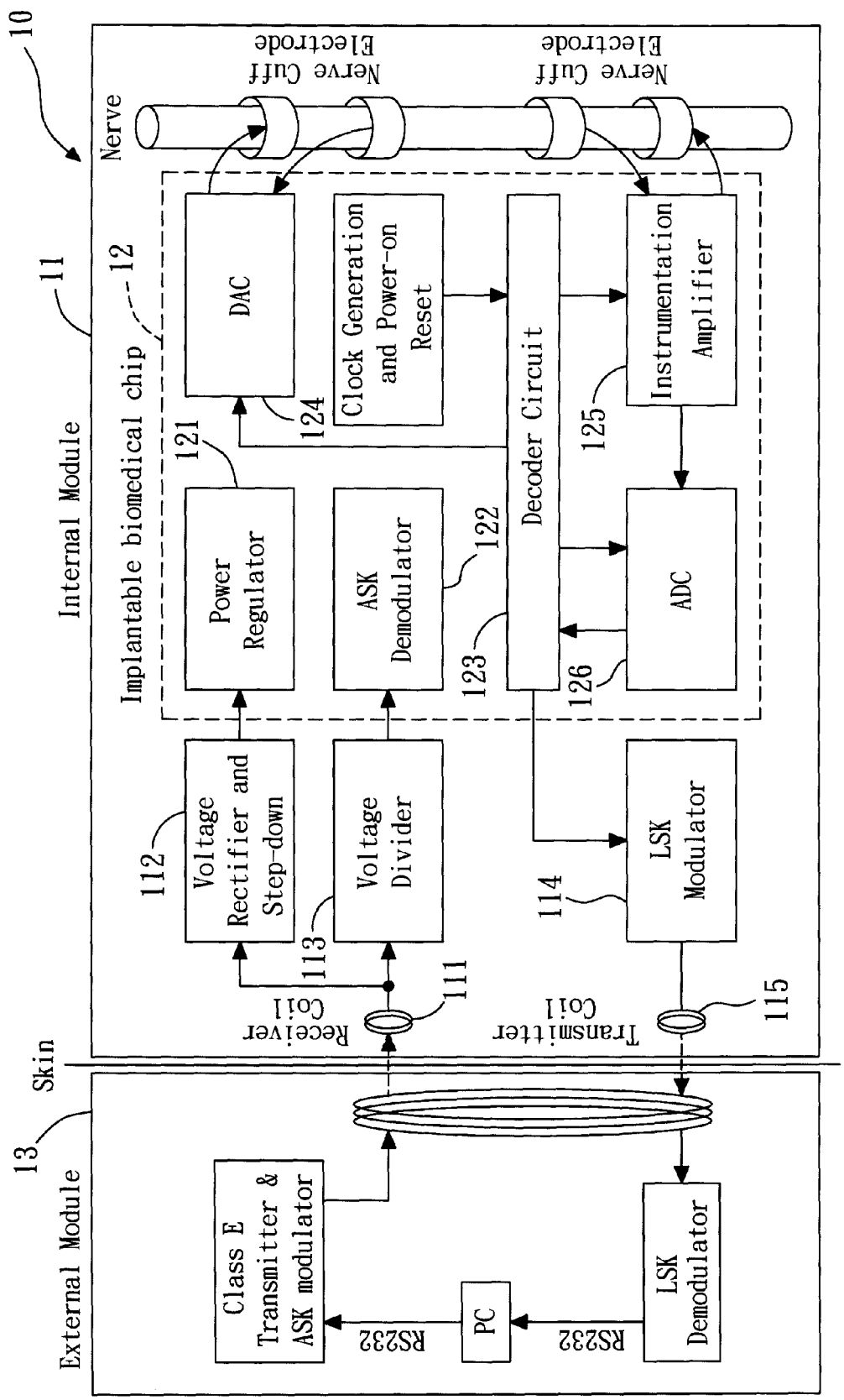
FIG. 1 shows a conventional wireless neural stimulating system.
Figure 2:
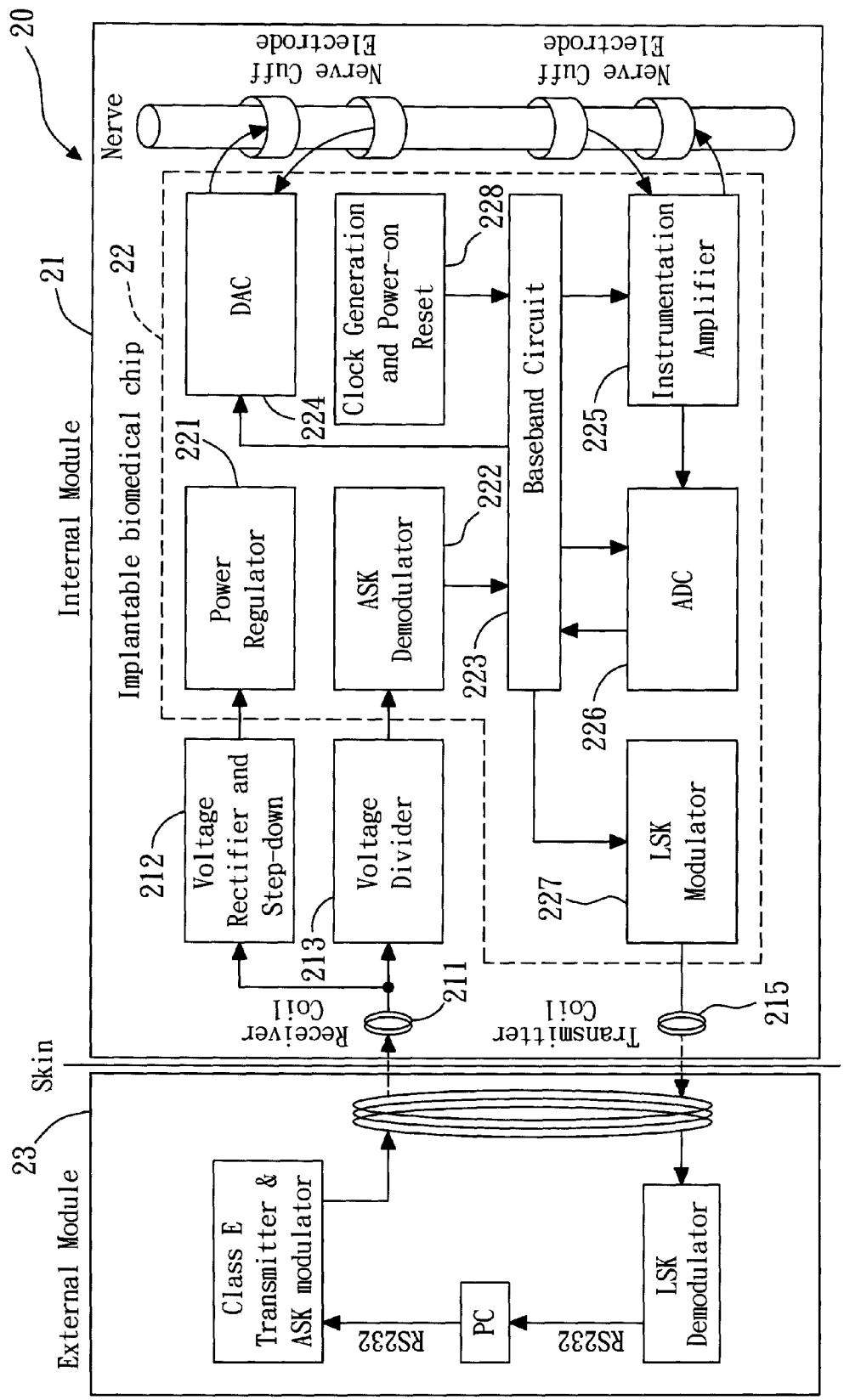
FIG. 2 shows a wireless neural stimulating system with an implantable biomedical chip having load-shift keying (LSK) modulator according to the invention.

Referring to FIG. 2, it shows a wireless neural stimulating system with an implantable biomedical chip having load-shift keying modulator, according to the invention. The wireless neural stimulating system 20 comprises: an internal module 21 and an external module 23. The internal module 21 is implemented in the body. The internal module 21 comprises a receiver coil 211, a voltage rectifier and steps-down circuit 212, a voltage divider 213, a transmitter coil 215 and an implantable biomedical chip 22.

The implantable biomedical chip 22 comprises a power regulator 221, a demodulator 222, a baseband circuit 223, a D/A converter 224, an instrumentation amplifier 225, an A/D converter 226 and a modulator 227. The power regulator 221 is used for receiving power from the receiver coil 211 and providing power. The demodulator 222 is used for demodulating an input signal from the receiver coil 211 to a demodulated signal. The demodulator 222 may be an Amplitude Shift Keying (ASK) demodulator. The baseband circuit 223 is used for decoding the demodulated signal to at least one control signal. The D/A converter 224 is used for converting the control signal to a stimulating current to the nerve. The instrumentation amplifier 225 is used for amplifying and filtering a neural signal from the nerve. The A/D converter 226 is used for converting the neural signal from the instrumentation amplifier to a digital neural signal. The modulator 227 is used for modulating the digital neural signal to an output signal. The demodulator 227 may be a Load-Shift Keying (LSK) modulator. The output signal is transmitted to the external module 23 by the transmitter coil 215.

The implantable biomedical chip 22 further comprises a clock generator and power-on reset circuit 228, the clock generator used for generating a clock signal to the baseband circuit 223, the power-on reset circuit used for generating a power-on reset signal to the baseband circuit 223.

Figure 3:
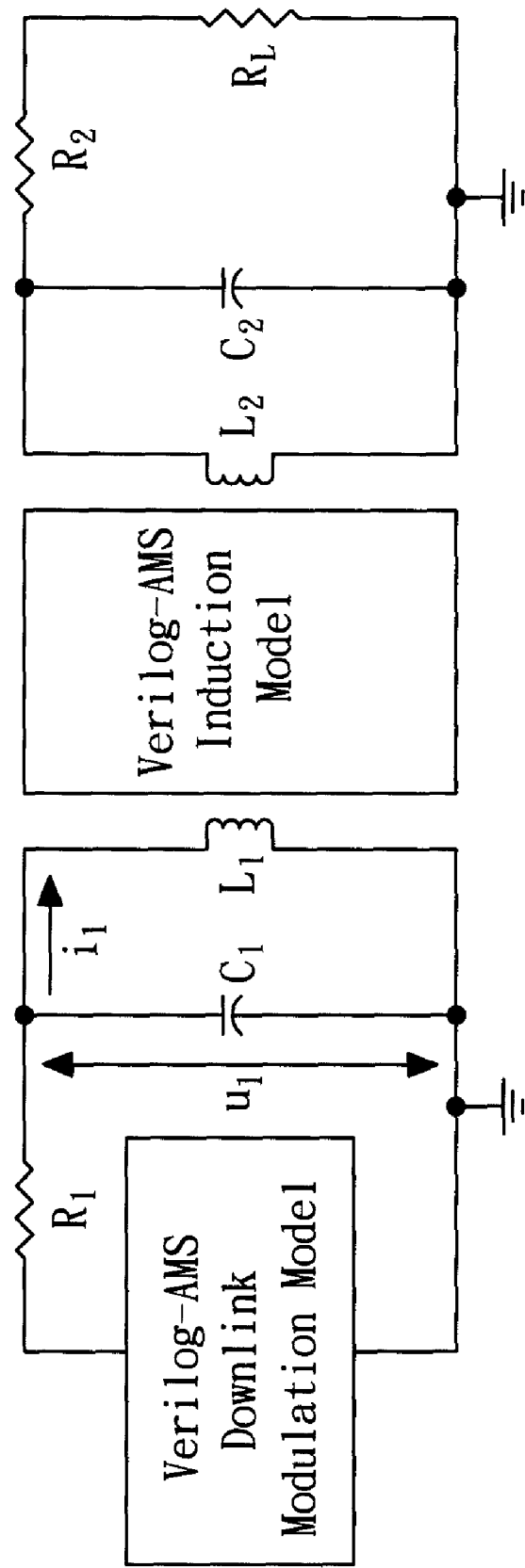
FIG. 3 shows the simplified simulation model of the bi-directional telemetry.

Referring to FIG. 3, it shows the simplified simulation model of the bi-directional telemetry. The first resistor $R_1$ includes the output resistor of the downlink modulator and the parasitic resistor. The first capacitor $C_1$ and the first inductance coil $L_1$ are the external resonant circuits, while the second capacitor $C_2$ and the second inductance coil $L_2$ are the internal resonant circuits. The second resistor $R_2$ is the parasitic resistor. The load resistor $R_L$ is the equivalent load resistor which represents how much power is consumed by the implantable biomedical chip 22.

According to the induction fundamental, the first voltage ($u_1$) in the external coil can be found by the multiplication of the current through the external coil and the induced impedance ($Z_T$), wherein $Z_T$ represents the feedback from the loading of the internal coil and appears as the impedance of the external coil. Thus, the first voltage $u_1$ is expressed by the following equation.

$$u_1 = i_1 \times Z_T = i_1 \cdot \frac{w^2 k^2 \cdot L_1 L_2}{R_2 + j\omega L_2 + Z_2} \quad (1)$$

where $Z_2 = \frac{R_L}{1 + j\omega R_L C_2}$, and $k$ is the coupling coefficient Because we don't care the phase response, the magnitude of the induced impedance is taken into consideration.

$$|Z_T| = \frac{w^2 k^2 \cdot L_1 \cdot L_2}{f_1^2 + f_2^2} \cdot \sqrt{(f_1 + f_2 \omega R_L C_2)^2 + (f_1 \omega R_L C_2 - f_2)^2} \quad (2)$$

where $f_1 = R_2 + R_L - w^2 R_L L_2 C_2$, and $f_2 = wL_2 + wR_2 R_L C_2$.

Figure 4:
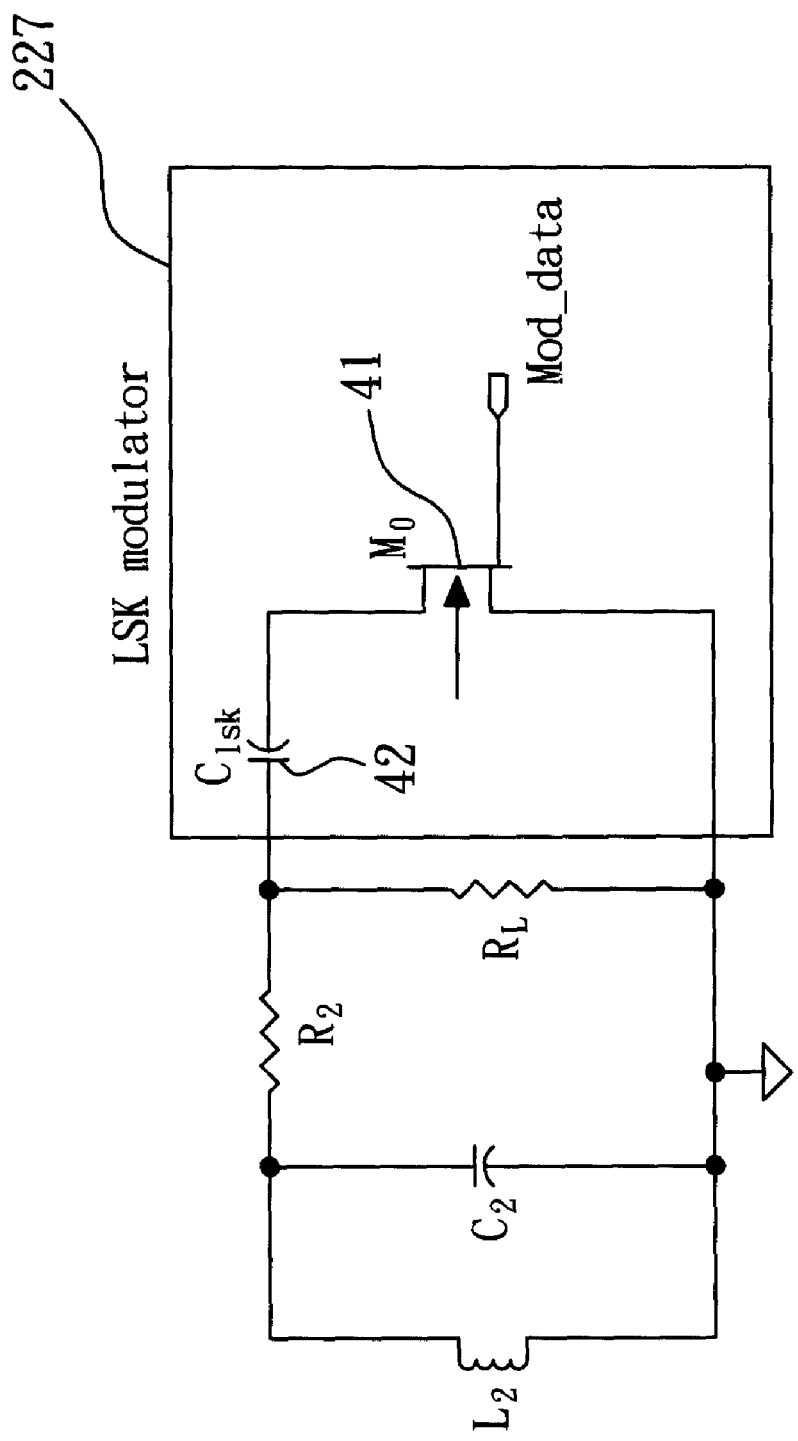
FIG. 4 shows a LSK modulation, according to the invention.

According to Eqn. (1) and Eqn. (2), it is derived that the amplitude of the first voltage $u_1$ can be determined by the load resistor $R_L$. However, changing the loading resistor $R_L$ would make change in power that is supplied for the implantable biomedical chip. Moreover, in order to make the voltage difference in the first voltage $u_1$ more obvious such that it can be detected more easily, a severe variation in $R_L$ is required. It may reduce the power supplied for the implantable biomedical chip. Thus, an on-chip switched-capacitor circuit is used as the LSK modulator 227 to vary the induced impedance $Z_T$, as shown in FIG. 4. The load-shift keying modulator 227 comprises: a transistor 41 and a capacitance 42.

Implementation and simulation of the invention include the mathematic model and the schematic circuit. Thus, we use Verilog-AMS, which is the extension of two languages, Verilog-HDL and Verilog-A, to model the induction formula described in the above and the operation of the external modulator. This work is simulated by using Spectre simulator. In the simulation, ASK modulation is used for downlink. The first voltage $u_1$ reflects the switch of the 2 pF capacitor in its amplitude. The amplitude variation of the first voltage $u_1$ is 24% and 2% when the voltage in the external coil is 460 Vp-p and 250 Vp-p, respectively. The parameters of the components in FIGS. 2 and 3 are shown in TABLE I. The power consumption of the LSK modulator is 0.95 mW at 10 Kbps data rate and the area is 50×90 μm².

TABLE I

| COMPONENT PARAMETERS OF STIMULATION | |
|---|---|
| Components | Value |
| $L_1$ | 28 μH |
| $L_2$ | 13.55 μH |

TABLE I-continued

| COMPONENT PARAMETERS OF STIMULATION | |
|---|---|
| Components | Value |
| $C_1$ | 226 pF |
| $C_2$ | 467 pF |
| $C_{lsk}$ | 2 pF |
| $R_1$ | 10 μΩ |
| $R_2$ | 10 μΩ |
| $R_L$ | 1 MΩ |
| K | 0.4 |
| ω | 12.56 Mrad/s |

According to the invention, the LSK modulator 227 can be included on the implantable biomedical chip 22, and can achieve full-duplex communication to improve the controllability and observability. Besides, the power consumption and area occupation is reduced as compared with the prior art using discrete components. Therefore, the integration of the implantable biomedical chip can be easily accomplished.

Figure 5:
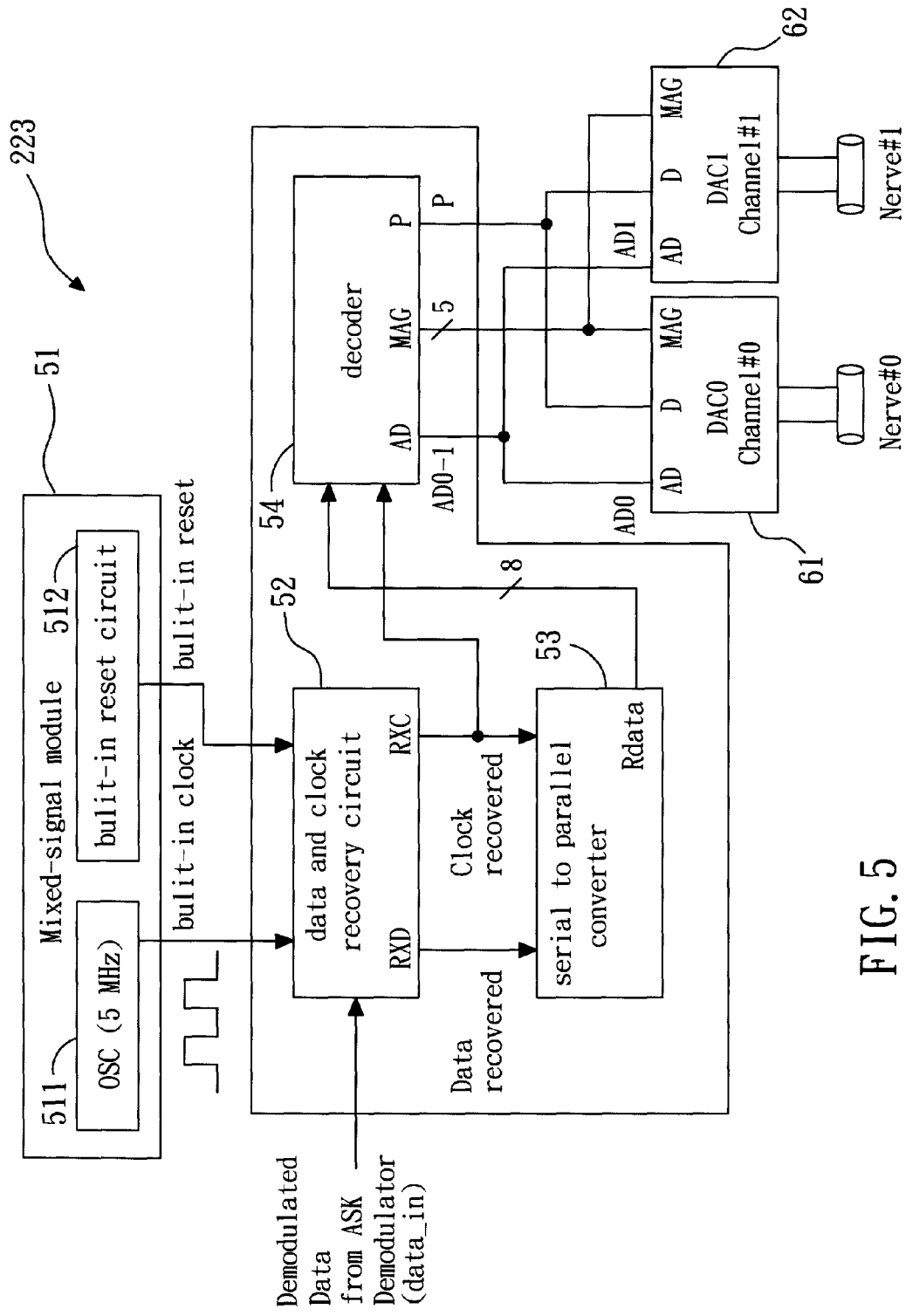
FIG. 5 shows a baseband circuit of the implantable biomedical chip, according to the invention.

Referring to FIG. 5, the baseband circuit 223 comprises: a mixed-signal module 51, a data and clock recovery circuit 52, a serial to parallel converter 53 and a decoder 54. The mixed-signal module 51 is used for generating a built-in clock signal and a built-in reset signal. The mixed-signal module 51 comprises: an oscillator (OSC) 511 and a built-in reset circuit 512. The oscillator 511 is used for generating the built-in clock signal (5 MHz), the built-in reset circuit 512 is used for generating the built-in reset signal.

The data and clock recovery circuit 52 is used for generating a recovered clock signal and recovering the demodulated signal from the ASK demodulator 222 to a recovered packet according to the built-in clock signal and the built-in reset signal. The serial to parallel converter 53 for converting the recovered packet into a parallel recovered packet. The decoder 54 is used for decoding the recovered clock signal and the parallel recovered packet and generating an address control signal (AD), a magnitude control signal (MAG) and a polarity control signal (P) to the corresponding D/A converter channels 61 or 62 of the D/A converter 224.

The D/A converter channels 61 or 62 of the D/A converter 224 directly supply stimulating currents to their associative nerves to serve as a stimulus. The magnitude of the stimulating current is determined by the magnitude control signal (MAG). The polarity control signal (P) is used to control the stimulating current direction. When AD=0, the stimulus for nerve #0 is activated.

Figure 6:
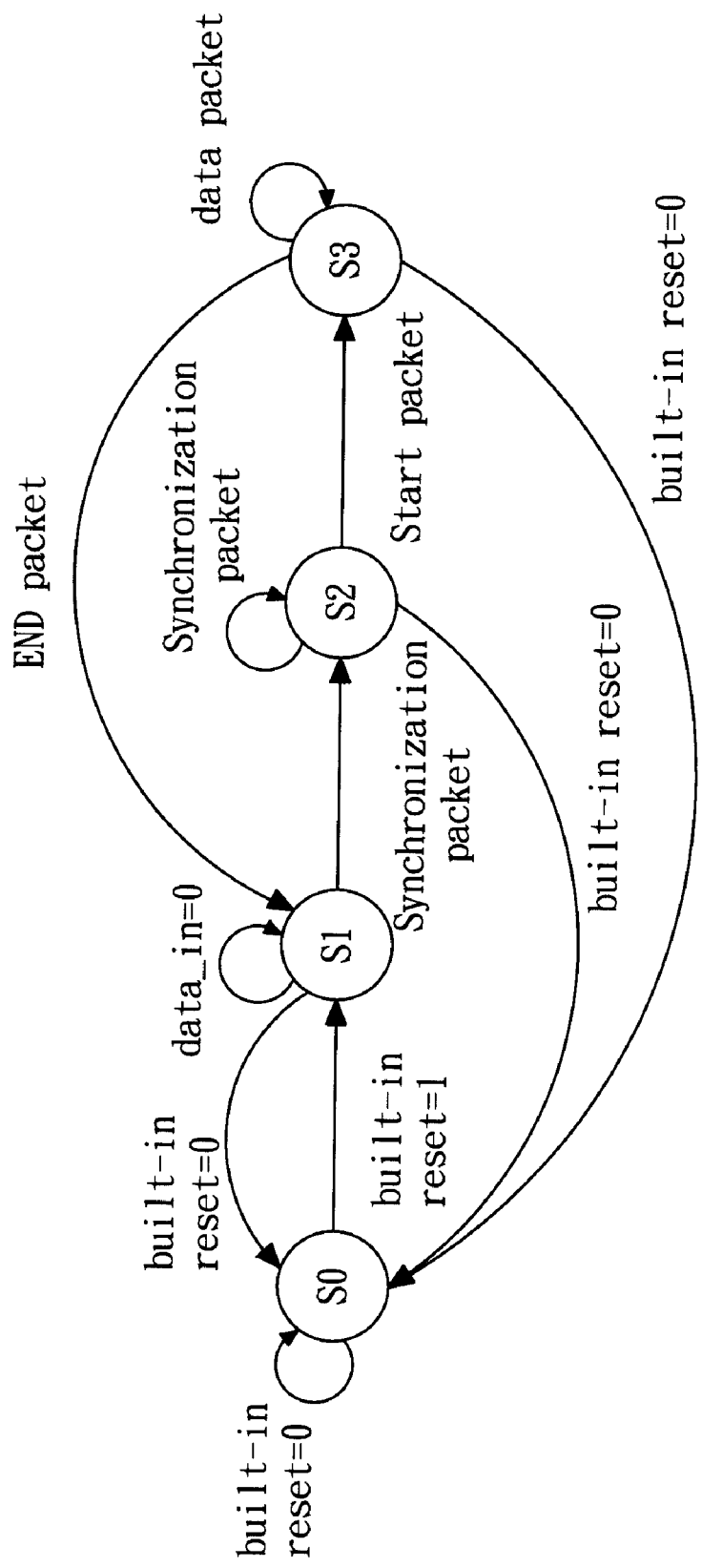
FIG. 6 shows a state transition method for the implantable biomedical chip according to the invention.

Referring to FIG. 6, it shows a state transition method for the implantable biomedical chip according to the invention. There are four states: a zero state S0, a first state 51, a second state S2 and a third state S3. Referring to FIG. 5 and FIG. 6, the built-in reset signal circuit 512 generates the built-in reset signal. The demodulated signal from the ASK demodulator comprises: a synchronization packet, a start packet, data packet and an end packet. When the built-in reset signal is at low level (0), the state does not transit and remain in the zero state S0. When the built-in reset signal is at high level (1), the zero state S0 is transited to the first state S1.

When the synchronization packet is received, the first state 51 is transited to the second state S2. When the built-in reset signal is at low level (0), the first state is transited to the zero state. If there is no data (data_in=0), the state does not transit and remain in the first state 51. When the synchronization packet is received, the data and clock recovery circuit 52 counts how many cycles of the 5 MHz built-in clock during each positive edge and negative edge of the synchronization packet. The cycle numbers are recorded and then used to generate the system clock.

When the start packet is received, the second state S2 is transited to the third state S3. When the built-in reset signal is at low level (0), the second state S2 is transited to the zero state S0. If the start packet is not received, the state does not transit and remain in the second state S2.

When an end packet is received, the third state S3 is transited to the first state S1. When the built-in reset signal is at low level (0), the third state S3 is transited to the zero state S0. If the end packet is not received, the state does not transit and remain in the third state S3 for receiving data packets.

While an embodiment of the present invention has been illustrated and described, various modifications and improvements can be made by those skilled in the art. The embodiment of the present invention is therefore described in an illustrative, but not restrictive, sense. It is intended that the present invention may not be limited to the particular forms as illustrated, and that all modifications which maintain the spirit and scope of the present invention are within the scope as defined in the appended claims.

What is claimed is:

1. A state transition method for an implantable biomedical chip, comprising the steps of:
   (a) transiting a zero state to a first state according to a built-in reset signal;
   (b) transiting the first state to a second state according to a synchronization packet;
   (c) transiting the second state to a third state according to a start packet; and
   (d) transiting the third state to the first state according to an end packet.

2. The state transition method according to claim 1, wherein when the built-in reset signal is at high level, the zero state is transited to the first state.

3. The state transition method according to claim 1, further comprising a step of: transiting the first state to the zero state when the built-in reset signal is at low level.

4. The state transition method according to claim 1, further comprising a step of: transiting the second state to the zero state when the built-in reset signal is at low level.

5. The state transition method according to claim 1, further comprising a step of: transiting the third state to the zero state when the built-in reset signal is at low level.

* * * * *